United States Patent [19]

Schontzler et al.

[11] 4,022,059
[45] May 10, 1977

[54] FLOW AND TIME PROPORTIONAL SAMPLING SYSTEM

[75] Inventors: J. Gordon Schontzler; Wendall C. Gates, both of Santa Cruz, Calif.

[73] Assignee: Manning Environmental Corporation, Santa Cruz, Calif.

[22] Filed: Aug. 15, 1974

[21] Appl. No.: 497,569

Related U.S. Application Data

[63] Continuation-in-part of Ser. No. 455,879, March 28, 1974, abandoned.

[52] U.S. Cl. .................................. 73/198; 73/206; 73/215; 73/421 B; 141/130
[51] Int. Cl.$^2$ ...................... G01F 1/02; G01N 1/14
[58] Field of Search ....... 73/421 R, 421 B, 422 TC, 73/215, 216, 206, 198; 33/126.5, 126.6; 141/130

[56] References Cited

UNITED STATES PATENTS

| | | | |
|---|---|---|---|
| 2,414,086 | 1/1947 | Brewer | 73/206 |
| 2,657,577 | 11/1953 | Falk | 33/126.5 |
| 2,692,820 | 10/1954 | Alway et al. | 73/23.1 |
| 2,880,764 | 4/1959 | Pelarin | 141/130 |
| 3,040,585 | 6/1962 | Chatel et al. | 73/453 |
| 3,124,000 | 3/1964 | Melas | 73/215 |
| 3,719,081 | 3/1973 | Lynn et al. | 73/421 B |
| 3,751,990 | 8/1973 | Blechman | 141/130 |
| 3,795,347 | 3/1974 | Singer | 222/21 |
| 3,838,719 | 10/1974 | Lederer | 141/284 |
| 3,866,028 | 2/1975 | Schontzler | 73/215 |
| 3,896,673 | 7/1975 | Audouze | 73/421 B |
| 3,915,011 | 10/1975 | Nelson | 73/421 B |
| 3,924,471 | 12/1975 | Singer | 73/421 B |
| 3,929,017 | 12/1975 | Kowalski | 73/198 |

FOREIGN PATENTS OR APPLICATIONS

720,161  12/1954  United Kingdom .............. 73/421 B

*Primary Examiner*—S. Clement Swisher

*Attorney, Agent, or Firm*—Flehr, Hohbach, Test, Albritton & Herbert

[57] ABSTRACT

A sampling system for drawing samples from a fluid flow which is responsive to manual actuation, predetermined increments of flow volume, or predetermined increments of time. The system includes a flow meter and a flow sampler interconnected and physically located in the vicinity of the flow being monitored. The flow meter converts the flow head to flow rate and subsequently to flow volume. The head to flow conversion is mechanical and provides for flow measurement through a flow channel having a given cross section shape over a wide range of shape sizes by means of an electrical adjustment. The flow meter provides for flow measurement through flow channels having varying cross secton shapes by means of selectively engaging a predetermined one of a plurality of cams designed to convert head to flow is being measured. The sampler is electrically connected to the flow meter for use in the sample per flow volume mode and provides for a constant volume sample which is independent of flow head, sampler height above the flow surface, power source voltage level, pumping time or any of the other variables which heretofore affected the sample volume. Automatic sequencing within the sampler provides for purging the system, drawing the sample from the flow, sizing the sample, depositing the sample in a storage container, and purging the sampler intake after storage. Means are provided for depositing a predetermined number of samples in each of a plurality of storage containers, or for utilizing a predetermined number of containers for holding each sample, and for de-energizing the sampler until manually attended after a predetermined number of storage containers have received samples. The automatic internal sampler sequencing is initiated by an input signal which is generated by either a flow or time proportional sensor or manual actuation according to control selection.

47 Claims, 14 Drawing Figures

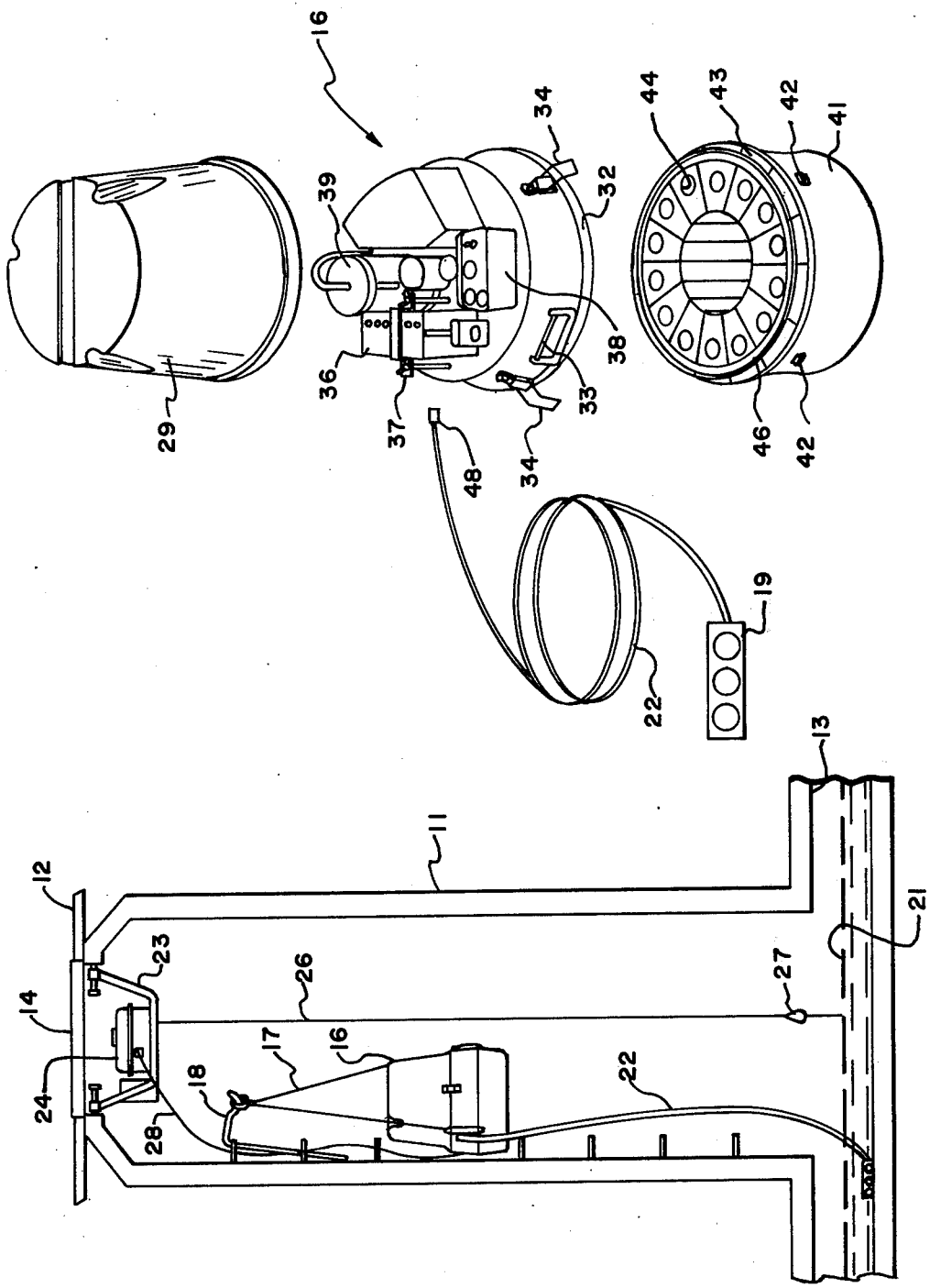

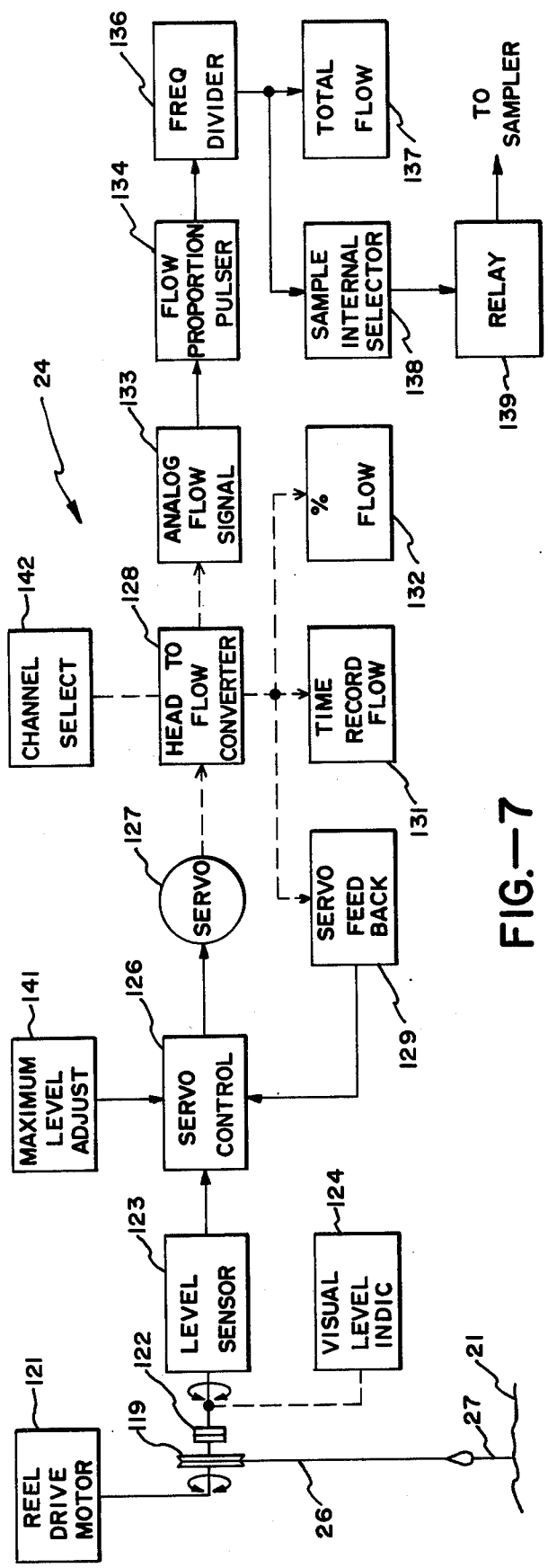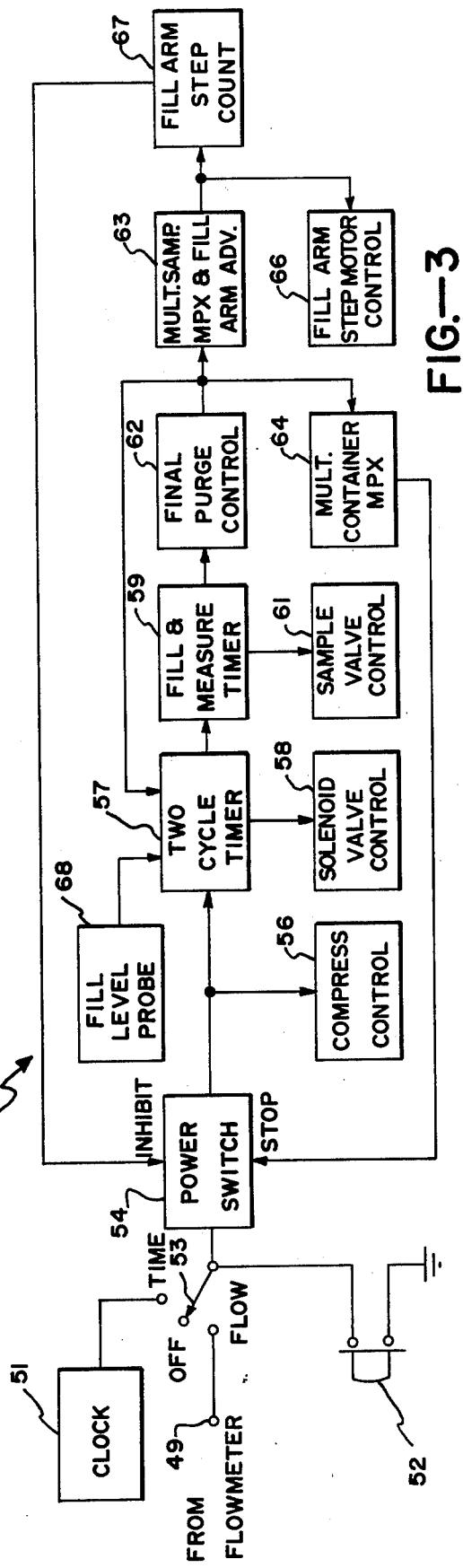
FIG.—7
FIG.—3

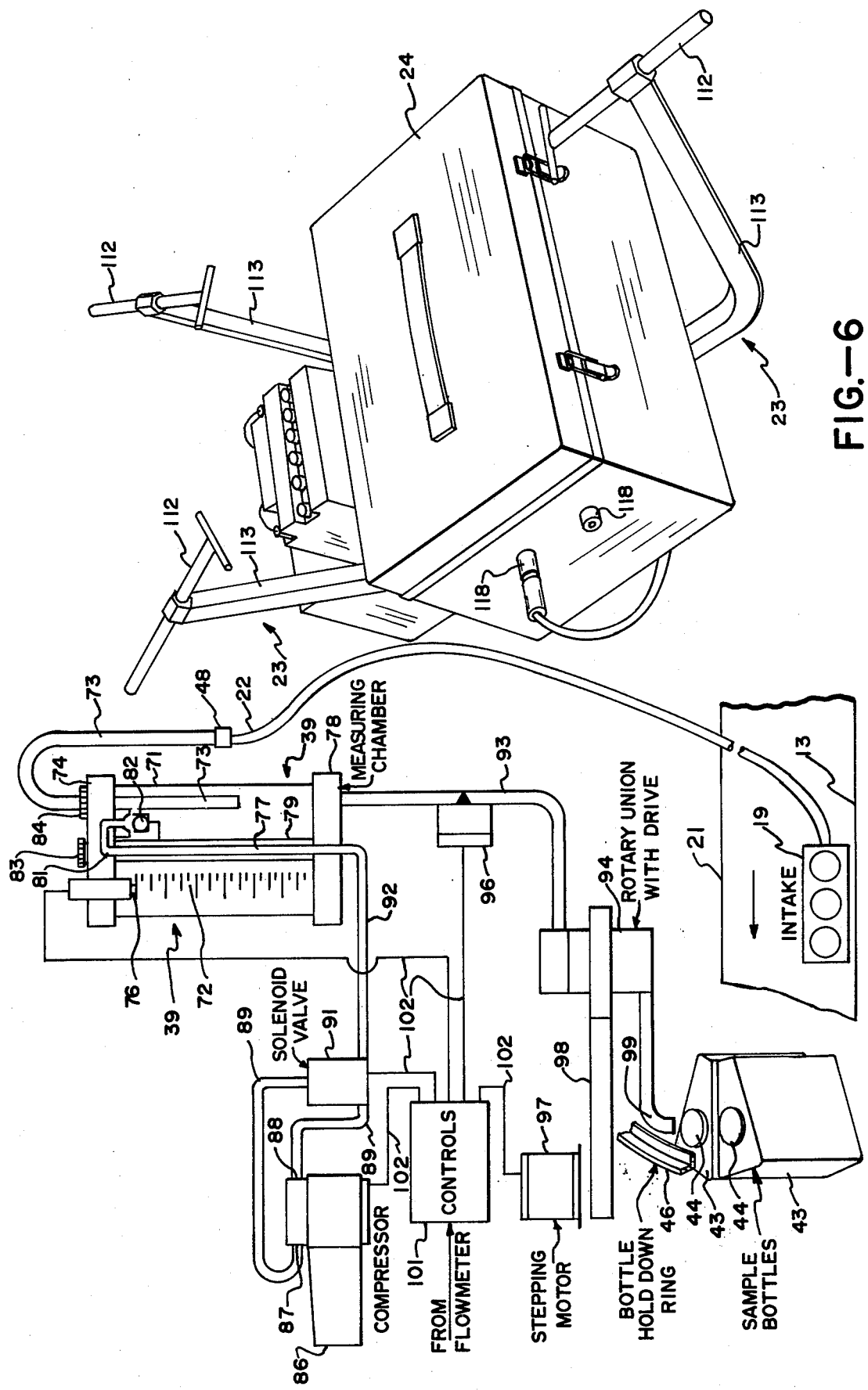

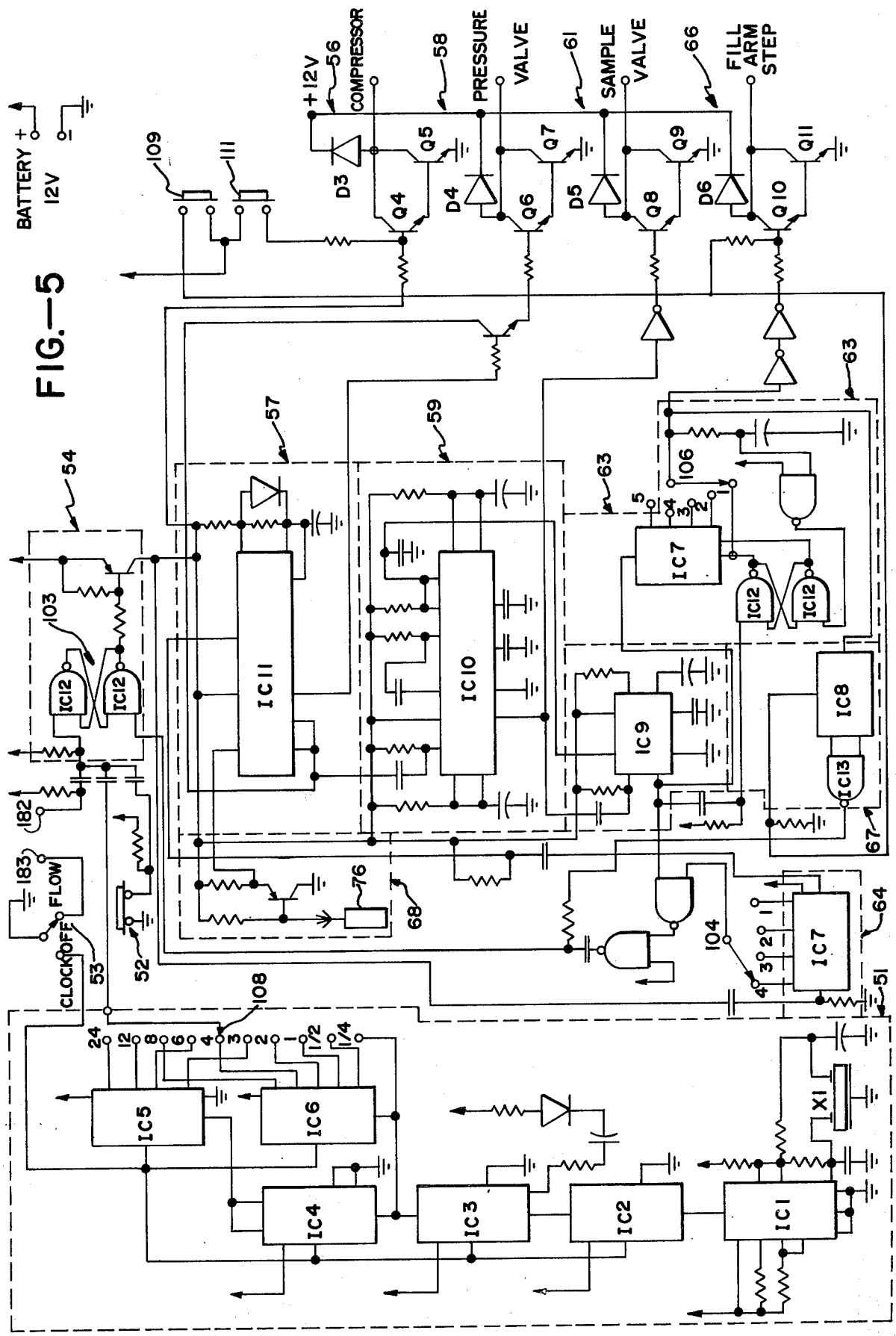

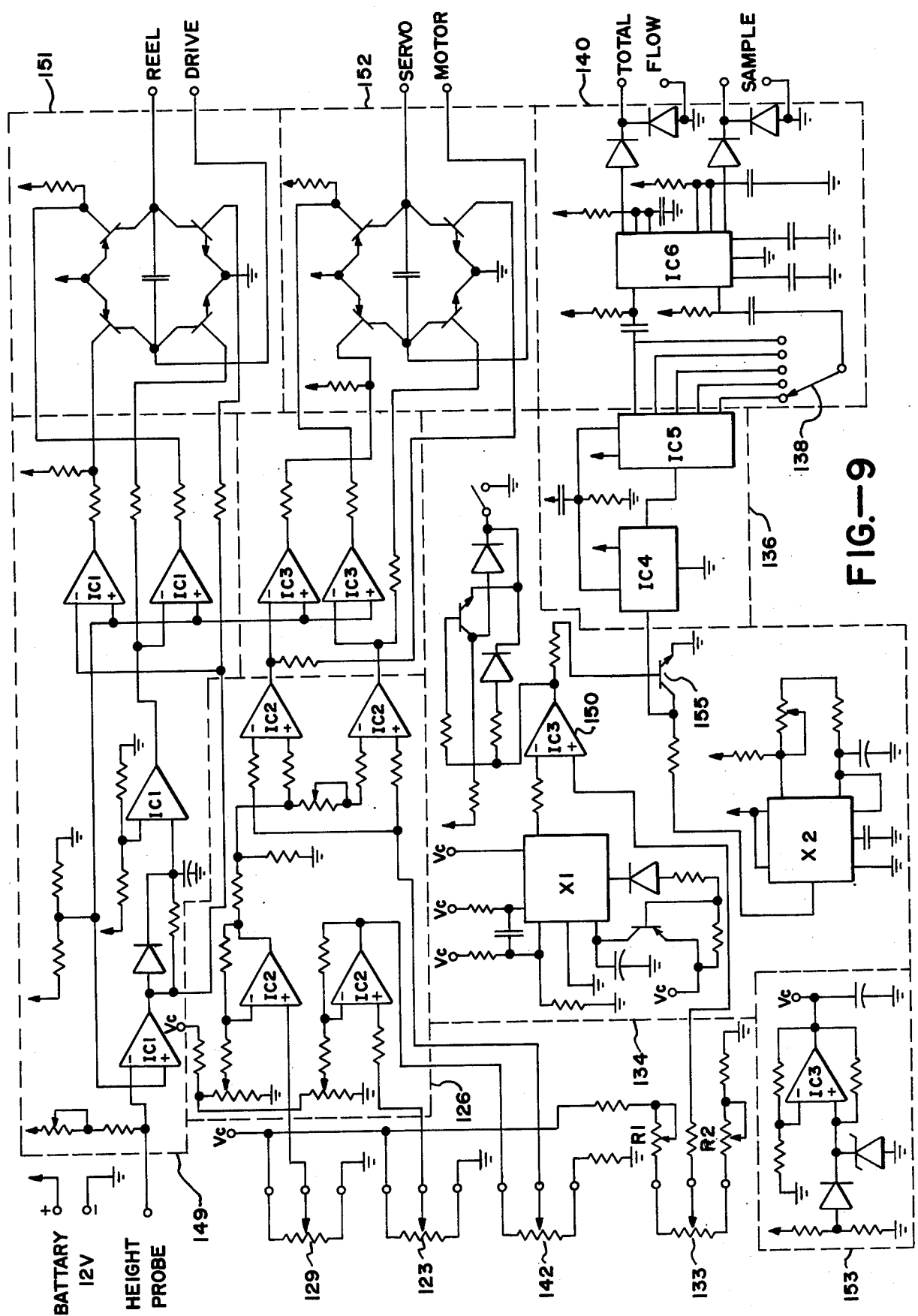
FIG.—9

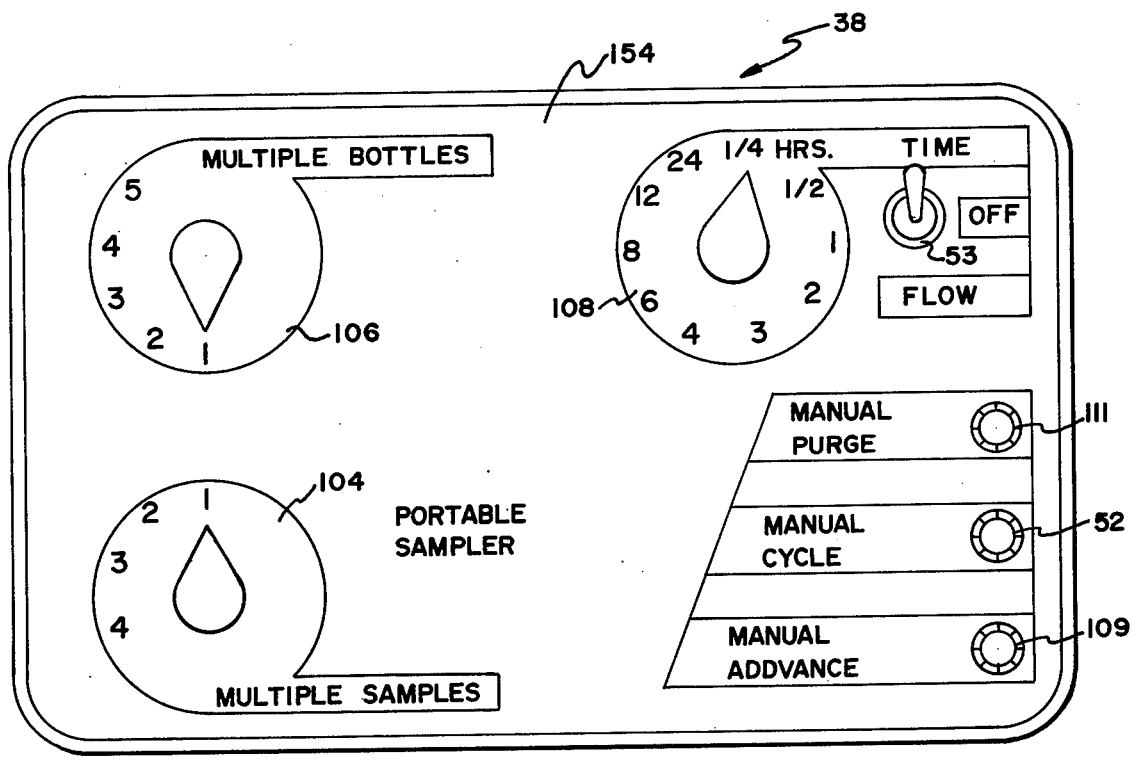
FIG.—10
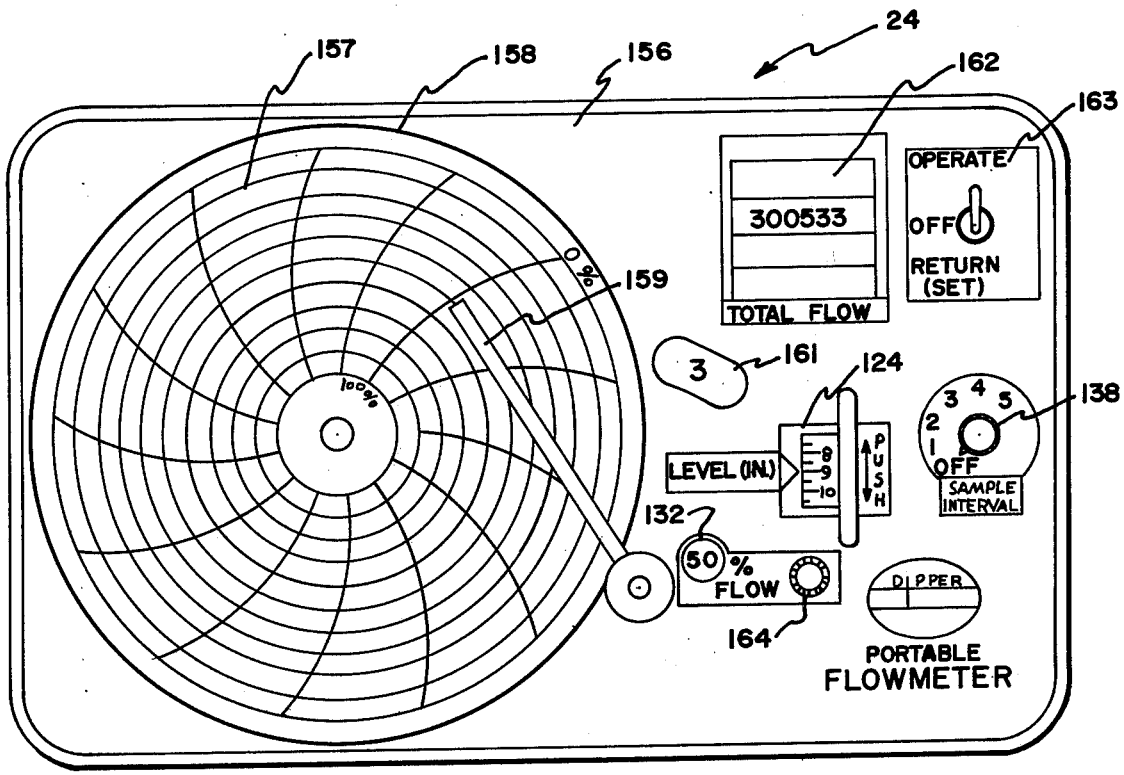
FIG.—11

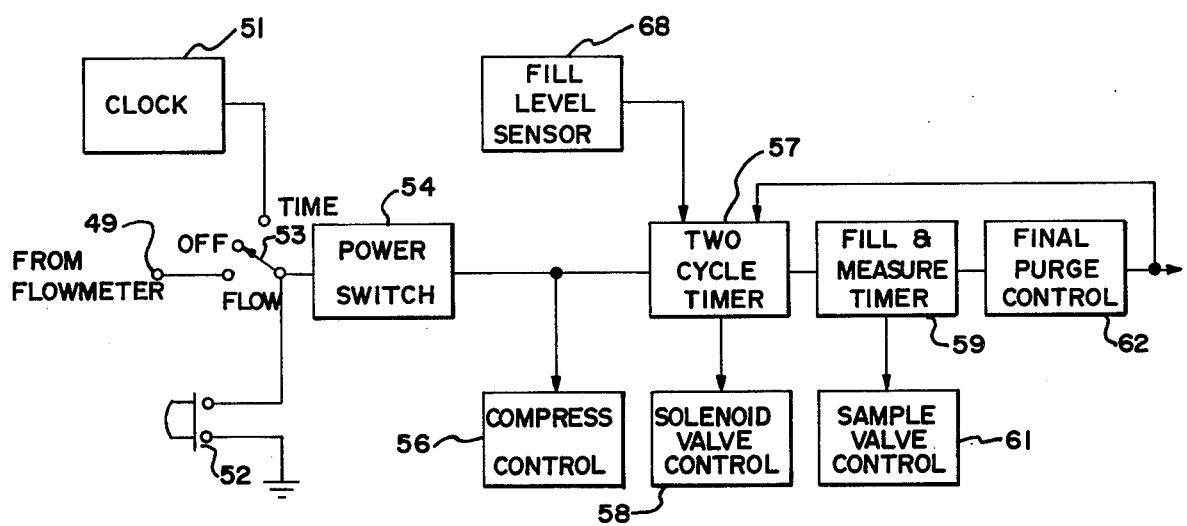
FIG.—12
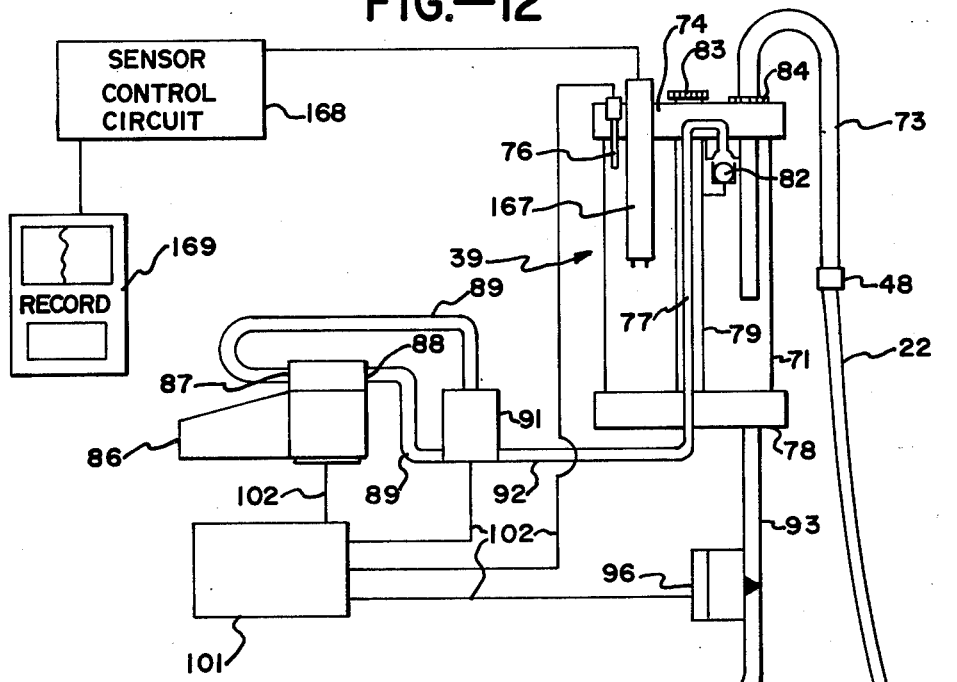
FIG.—13
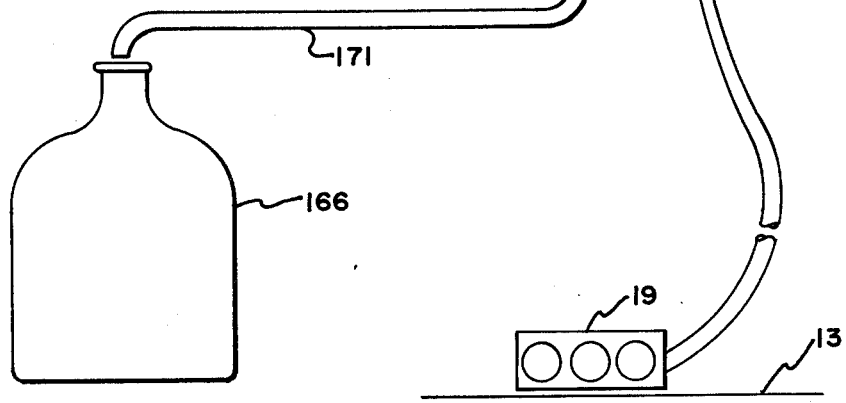

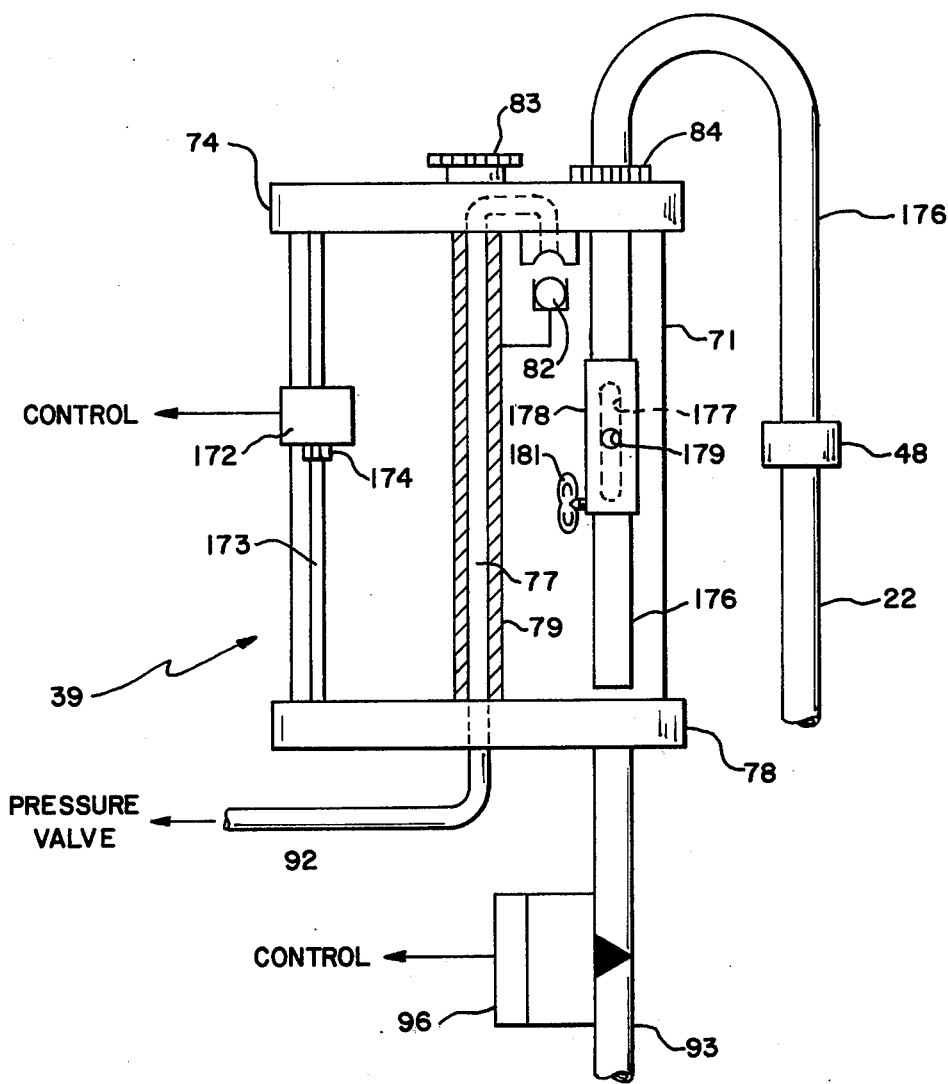
FIG.—14

FLOW AND TIME PROPORTIONAL SAMPLING SYSTEM

CROSS REFERENCE

This application is a continuation-in-part of copending application Ser. No. 455,879, filed Mar. 28, 1974, now abandoned.

BACKGROUND OF THE INVENTION

The invention disclosed herein relates to sampling of a fluid flow which may proceed unattended for an extended period, and more particularly to a system for sampling which is proportional to either time or flow volume and which provides a predetermined sample volume of fluid which is truly representative of the actual fluid passing through the flow channel.

Flow meters in the past for use with flow sampling systems have been of the type providing questionable flow volume accuracy due to known deficiencies in the flow sensitive structure and due to clogging which occurs in impeller, orifice, or venturi type flow measurement devices. Moreover, samplers for operation in conjunction with such flow meters are subject to internal corrosion, clogging, variation in sample size and misrepresentative sample draw, which leaves subsequent analysis of samples taken as questionable means for determining the true character of the flow sampled. Samplers for use in circumstances requiring samples to be drawn per increment of time are generally not adaptable for use where samples are desired at increments of flow volume through the flow channel.

There is therefore a need for a flow and time proportional sampling system which may be used in either set of circumstances by merely pre-setting controls, or which may be operated manually if desired. Accurate and representative samples are needed for meaningful monitoring of the characteristics of the fluid flow.

SUMMARY AND OBJECTS OF THE INVENTION

A flow and time proportional sampling system is disclosed which provides stored samples for subsequent analysis utilizing a fluid flow sampler which provides a sampling sequence initiated by an appropriate input signal. The input signal may be provided by an integral timer for time base sampling, by manual actuation of an associated switch, or by a fluid flow meter for flow volume base sampling. The flow meter senses fluid head in a flow channel and containes a servoed mechanical head to flow converter with multiple channel cross section shape and size measuring capabilities. The sampling sequence includes initial actuation by the input signal of a compressor for providing a positive and negative pressure source. A timed sequence is also initiated by the input signal. The timed sequence includes chamber purging, chamber filling, sample sizing, sample storage, and sequence resetting to place the system in a ready condition to receive the ensuing input signal.

It is an object of the present invention to provide a flow proportional sampling system which makes possible an accurate quantitative and qualitative effluent measurement.

Another object of the present invention is to provide a flow proportional sampling system having controls for accommodating accurate flow measurement through channels of various cross sectional shapes and various cross section dimensions within any general cross sectional shape.

It is another object of the present invention to provide a flow proportional sampling system indicating instantaneous flow rate as well as total flow.

It is another object of the present invention to provide a fluid flow sampling system which is portable and easy to install.

It is another object of the present invention to provide a fluid flow sampling system which draws fluid samples in seconds for obtaining a truly representative flow sample.

It is another object of the present invention to provide a fluid flow sampling system which provides a constant sample size independent of intake dimensions, power source voltage, flow head, or the like.

It is another object of the present invention to provide a fluid flow sampling system which is self-purging.

It is another object of the present invention to provide a fluid flow sampling system which stores the flow samples in individual storage containers or a single storage container as desired.

It is another object of the present invention to provide a fluid flow sampling system with multiplexing capability for either storing a predetermined number of samples in each storage container, or a given sample in a predetermined number of storage containers.

It is another object of the present invention to provide a fluid flow sampling system which is time proportional for obtaining samples from the fluid flow at predetermined increments of time.

It is another object of the present invention to provide a fluid flow sampling system having a sampling sequence which may be initiated manually.

It is another object of the present invention to provide a fluid flow sampling system which is de-energized until attended after receiving a predetermined number of samples, thereby preventing adulteration of previously received samples.

Additional objects of the present invention will become apparent by reference to the following description of the invention and the associated drawings.

BRIEF DESCRIPTION OF THE DRAWINGS

FIG. 1 is a sectional view of a flow and time proportional sampling system installed in a sewer riser.

FIG. 2 shows an isometric exploded view of a portable sampler.

FIG. 3 is a block diagram of the sampler.

FIG. 4 is a mechanical schematic of the sampler of FIGS. 2 and 3.

FIG. 5 is an electrical schematic of the sampler.

FIG. 6 is an isometric view of a portable flow meter.

FIG. 7 is a block diagram of the flow meter.

FIG. 9 is an electrical schematic of the flow meter.

FIG. 10 is a plan view of the sampler control panel.

FIG. 11 is a plan view of the flow meter control panel.

FIG. 12 is a block diagram of an additional sampler embdiment.

FIG. 13 is a mechanical schematic of the sampler of FIG. 12.

FIG. 14 is a mechanical schematic of another sample chamber embodiment.

DESCRIPTION OF THE PREFERRED EMBODIMENTS

Figure 8:
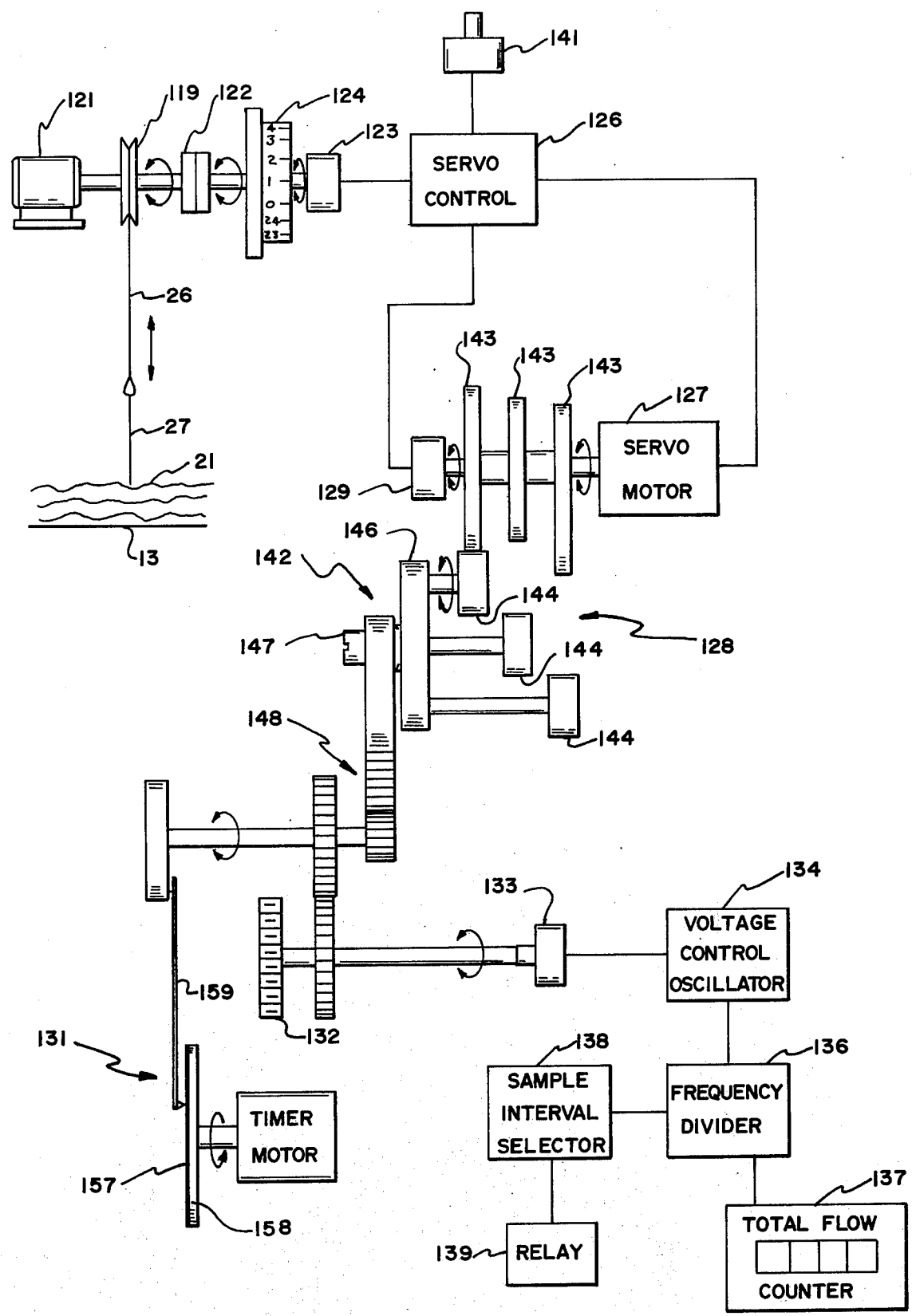
FIG. 8 is a mechanical schematic of the flow meter of FIGS. 6 and 7.

Fluid flow sampling systems are now items of major importance for industrial process monitoring in view of recent legislation for environmental control purposes. A system for providing sampling in response to predetermined flow volume passage in an open flow channel is seen in FIG. 1. As depicted there, the system is mounted in a sewer riser 11 extending between a street level 12 and a sewer flow channel 13. A manhole cover 14 covers the top of the sewer riser 11. A flow sampler 16 is suspended by means of a harness 17 from means such as hook 18 attached to the inside wall of sewer riser 11. An intake 19 is submerged in a body of fluid 21 passing through the sewer channel 13. A tube 22 is used to communicate intake 19 with the interior of the sampler 16.

Suspended in a mount 23 immediately beneath the manhole cover 14 is a flow meter 24. Flow meter 24 has depending therefrom a cable 26 on the end of which is attached a probe 27 for contacting the surface of flow 21. Means for providing an electrical connection between flow meter 24 and sampler 16 is seen in an electrical cable 28 therebetween.

Turning now to FIG. 2, the structural characteristics of sampler 16 will be described. A top cover 29, which may be of vacuformed plastic, is formed with depressions 31 therein to accommodate passage of the strands in the harness 17. A base plate or framework 32 is formed to receive the cover 29 and appears in this embodiment as an inverted circular pan. Base plate 32 has attached about the periphery conveniently located handles 33 and latches 34. Mounted on top of base plate 32 is a wet cell storage battery 36 retained thereon by a bracket 37. A control module 38 is mounted adjacent to battery 36 on base plate 32. A sample chamber assembly 39 is also mounted on base plate 32.

Sample storage means 41 is formed for mounting below base plate 32 having thereon hooks 42 for engagement by latches 34. The embodiment in FIG. 2 shows a plurality of wedge shaped storage containers 43 having open upwardly extending openings 44 positioned at a common radius from the center of storage means 41. A hold down ring 46 is disposed in sample storage means 41 to secure sample storage conrainers 43 therein. Intake 19 is shown on one end of tube 22, which in this instance is a pliable plastic tube of approximately ⅛ inch diameter having an adapter 48 on the other end thereof.

Sampler 16 is seen in block diagram form in FIG. 3. An input signal for initiating the sampler cycle may be received from a suitable source. The signal may be received from a flow meter at terminal 49, a clock 51 or may be provided manually by means such as manual switch 52.

The type of cycle control is adjusted at a mode switch 53 having in this embodiment positions designated as "time", "off", and "flow". Clock 51 is attached to the pole of mode switch 53 which is designated "time", a flow meter is attached to the pole of mode switch 53 designated "flow" and an open position of mode switch 53 is provided for "off" selection. Mode switch 53 is connected to the initiate or start terminal of a power switch 54. Manual switch 52 is also connected to the start terminal of power switch 54. Power switch 54 provides an output for energizing a compressor control 56 and for initiating a two-cycle timer 57. Two-cycle timer 57 is connected to provide signals to a solenoid valve control 58 and to a fill and measurement timer 59. Output signals from fill and measurement timer 59 are directed to a sample valve control 61 and a final purge control timer 62. The output from final purge control timer 62 is directed to reset two-cycle timer 57, and to a multiple sample multiplexing and filling arm drive circuit 63 for providing a predetermined number of samples to be stored in a single storage container such as bottles 43. The output of final purge control timer 62 is also directed to a multiple container multiplexing circuit 64 for providing a predetermined number of storage containers or bottles 43 to receive portions of a single sample. The multiple container multiplexing circuit 64 produces an output which is connected to the power switch 54 for stopping the power cycle. The multiple sample multiplexing circuit 63 provides an output which is directed to a stepper motor control 66 which provides for one step advancement of a filling arm to be hereinafter described. Multiple sample multiplexing circuit 63 also has its output connected to a step count circuit 67. The output of step count circuit 67 is directed to the power switch 54 for inhibiting power turn-on after a predetermined number of steps have occurred. Two-cycle timer 57 has a purge and a fill signal included in each of the cycles. An additional input to timer 57 provides for terminating the fill signal and eliminating the second cycle output from two-cycle timer 57 prior to the end of the fill portion of the first cycle. A fill level probe 68 provides this last named input to timer 57.

A mechanical description of one embodiment of the sampler may be seen in FIG. 4. Sample chamber assembly 39 includes a cylindrical clear wall 71 having visible graduations 72 marked on the side. A vertically adjustable pipe 73 extends through a top cover 74 on cylinder 71 depending therefrom inside chamber 39. Pipe 73 has an inverted U-shape and is connected to tube 22 leading to intake 19 on the end exterior of sampler chamber 39. In this embodiment electrical contact means 76 is mounted within chamber 39 and is positioned therein to complete an electrical circuit through a contained sample. Contact means 76 functions to sense when the sample chamber 39 is filled to a predetermined level. Other well known means for sensing fill level, such as capacitive sensors, ultrasonic transmission characteristic sensors, or sample weight sensors for example, may be used in place of contact means 76.

Sample chamber assembly 39 has a pressure inlet tube 77, which in this case is electrically conductive, extending through a sample chamber base 78, and encased in insulating material 79 within the chamber 39. Insulating material 79 isolates pressure inlet tube 77 from the sample in chamber 39 up to the predetermined fill level, in this embodiment, so that electrical contact means 76 is not rendered ineffective by a fault circuit completion through structural parts of the sampler. The sensing circuit for predetermined fill level includes that portion of the pressure inlet tube 77 extending above insulating material 79.

Inlet pressure tube 77 is in communication with a passage 81 through top cover 74 which leads into the interior of sample chamber 39. A ball check valve 82 is positioned at the point where passage 81 enters sample chamber 39 at a level above the contact level for electrical contact means 76. Means are provided for retaining top cover 74, cylinder 71 and sample chamber base 78 together such as a through stud (not shown) engaged by a knurled nut 83. Any suitable means may be used to retain vertically adjustable clamp 84.

A compressor 86 has a positive pressure port 87 and a negative pressure port 88. Pressure lines 89 are connected between compressor 86 and a pressure control valve 91. An additional pressure line 92 connects pressure control valve 91 to inlet pressure tube 77 in the sample chamber assembly 39.

A sample outlet line 93 extends through sample chamber base 78 extending to a sealed rotary union 94. A sample control valve 96 such as the pinch valve shown in FIG. 4 is located in sample outlet line 93, in this embodiment, just below the sample chamber assembly 39. A stepping motor 97 is connected through gearing 98 to the rotary union 94 to cause rotation of the lower portion thereof with respect to the upper portion. A spout or fill arm 99 extends from a lower portion of union 94 having a radius sufficient to convey samples to a point overlying openings 44 in storage container bottles 43.

A control module 101 is electrically connected by conductors 102 to compressor 86, pressure control valve 91, sample control valve 96 and stepping motor 97 as seen in FIG. 4. Control module 101 contains circuitry which may be seen by referring to FIG. 5. As seen therein, the clock 51 of FIG. 3 is shown enclosed in dashed lines. Mode switch 53 is shown positioned to select the signal to which the sampling cycle is responsive, time or flow. Manual switch 52 is also shown to provide a signal to initiate the sampling sequence. The selected signal initiating the sampler cycle is delivered to the power switch 54 which contains an initiate latch shown generally at 103 for turning on power circuit 54. Power circuit 54 is shown with the output power connected to two-cycle timer 57 as well as to compressor control circuit 56. Two-cycle timer 57 is also electrically connected to pressure valve control 58 as well as to the sample chamber fill and measurement timer 59. Timer 59 is electrically connected to sample control valve drive 61 and the final purge timer 62. Timer 62 produces output which is electrically connected to two-cycle timer 57, for resetting the timer as well as to the multiple sample multiplex circuit 63 and the multiple container multiplex circuit 64. A control switch 104 may be seen for circuit 64 for selecting from one through four bottles 43 to receive portions of a given sample. Another switch 106 is available at circuit 63 to select a predetermined number of samples, from one through five, to be deposited in each bottle 43. The output of multiple sample multiplexer and fill arm advance circuit 63 is connected to the circuit 66 for controlling the step advancement of rotatable filling arm 99. The multiple sample and fill arm advance circuit 63 provides an output connected to the fill arm step count circuit 67 which is seen to be connected to the initiate latch 103 to inhibit power switch 54. The electrical contact means 76 in the fill level probe circuit 68 is connected to the two-cycle timer 57 to terminate the fill portion of the cycle when probe 76 contacts the surface of the sample in sample chamber 39.

Clock 51 includes a crystal oscillator 107 and a series of integrated circuits, IC2 through IC6, for providing a number of time interval selections for input to initiate latch 103 when the sampler is in the time mode. Switch 108 provides for the time interval selection. A manual fill arm advance switch is seen at 109 and a manual purge switch 111 is also included connected to provide power when actuated to fill arm step control circuit 66 and compressor control circuit 56 respectively.

The portable flow meter 24 is shown in FIG. 6 having means for support 23 in the form of three threaded adjustable mounting feet 112 passing through threaded holes in the ends of mounting support arms 113. Flow meter 24 is contained in a water-tight case having a lower portion 114 and a sealed cover 116 attached to the lower portion 114 by latches 117. Water-tight electrical feed-throughs 118 are located on one side of the flow meter lower case 114.

FIG. 7 is a block diagram of the flow meter 24 and includes probe 27 suspended from a reel 119 cable 26. Probe 27 and cable 26 form part of an electrical circuit and provide an electrical ground therefor when probe 27 contacts flow 21 in a flow conduit such as sewer channel 13. Reel 119 is driven by a reel drive motor 121. Reel 119 is also connected through a clutch 122 to a fluid level sensor 123 which senses the relative head of the flow 21. A visual level indicator 124 is also driven through clutch 122. Head sensor 123 provides an electrical output related to head in the flow channel 13 which is connected to a servo control 126. Servo control 126 drives a servo motor 127 which is mechanically connected to drive a head to flow converter 128. Head to flow converter 128 mechanically drives a servo feedback pot 129, a pen chart recorder 131 providing a time record of flow, and a visual indicator 132 providing a percentage maximum flow rate indication.

FIG. 7 also shows an analog flow signal control 133 which may be a potentiometer driven by the head to flow converter 128 and providing an output voltage connected to a flow proportional pulser 134. Pulser 134 may be a voltage controlled oscillator, but is a gated oscillator in the preferred embodiment. Pulser 134 provides a number of output pulses which are connected to a frequency divider 136 for providing a smaller number of output pulses which is proportional to the number of input pulses. The output pulses from frequency divider 136 are adjusted as will be hereinafter described to provide an indication of flow quantity at a total flow meter 137 in minutes of full flow through channel 13. The output from frequency divider 136 is also directed to a sample interval selector 138 which provides an output signal at preselected increments of total flow. The output signal from sample interval selector 138 is connected to a relay 139. Relay 139 closes a circuit which provides a signal which may be connected to sampler 16 for initiating a sampling sequence when sampler 16 is in the flow mode.

A maximum level adjust 141, or gain adjust, is provided for adjusting the gain or servo control 126. Flow meter 24 includes a plurality of head to flow conversion means 128 which may be selected by a channel selecting means 142 to correspond to a specified cross section of flow channel 13.

The mechanical interrelationship of the principal components included in flow meter 24 are shown in FIG. 8. The reel 119 and the drive motor 121 therefor are seen with cable 26 supporting probe 27 depending therefrom in contact with the surface of fluid flow 21. The visual level indicator dial 124 is seen driven by motor 121 through clutch 122. The same means is used for driving level sensor 123 which in this embodiment is a potentiometer having an output connected to servo control 126. Maximum level adjust 141 is also a potentiometer having an output connected to servo control 126. Servo motor 127 is driven by control 126 and in turn drives head to flow converter means 128 which in this embodiment takes the form of cams 143. The shaft upon which cams 143 are mounted drives the servo feedback potentiometer 129 for closing the loop about servo control 126. Cam followers 144 are mounted on a rotatable disc 146 which may be rotated by a slotted disc 147 which enters detents to assume pre-selected angular positions. Slotted disc 147 and rotatable disc 146 comprise the channel selection means 142. The output of head to flow converter 128 is provided mechanically through a gearing arrangement shown generally at 148 to drive the arm of the pen recorder 131 which records percent of maximum flow rate and also to drive the visual indicator 132 which displays the instantaneous percentage of maximum flow existing in channel 13.

A shaft connected to gearing 148 drives the analog flow signal control 133 which in this embodiment is a potentiometer. Flow proportional pulser 134, frequency divider 136, total flow meter 137, and sample interval selector 138 are as described in FIG. 7 above.

FIG. 9 is an electrical schematic of the circuitry included in flow meter 24 and includes a dipper logic or liquid level sensing and seeking logic section 149 for receiving the indication of contact or no contact between probe 27 and the surface of flow 21. Dipper logic 149 is connected to a drive motor circuit 151 for reel 119 which provides an output to the reel drive motor 121 for elevating or lowering probe 27 depending upon whether probe 27 is or is not contacting respectively the surface of flow 21. Servo feedback potentiometer 129 is shown providing an input to servo control circuit 126. Level sensor potentiometer 123 is shown also providing an input to servo control circuit 126. Maximum level adjust potentiometer 141 in like manner provides an input to servo control circuit 126. The analog flow signal control 133 is shown in the form of a potentiometer having an output voltage connected to the input of flow proportional pulser 134. Pulser 134 produces a number of output pulses which are connected to frequency divider circuit 136 containing integrated circuit devices IC 5 and IC 6 for dividing the output of pulser 134. As seen in FIG. 9, the output of divider circuit 136 is directed to an output pulse shaping circuit 140 which provides flow proportional pulses to terminals connected to total flow meter 137. The output of output pulse shaping circuit 140 is also directed to sample interval selector switch 138 which provides for a sampling output at the end of multiples of 1, 2, 4, 8, or 16 predetermined time increments of full flow through channel 13. Switch 138 is then connected to relay 139 which, when energized produces an output signal indicative of a predetermined number of minutes of full fluid flow through channel 13.

The manner in which pulser 134 produces output pulses is described with reference to section 134 of FIG. 9. A ramp or sawtooth wave generator X1 having a positive slope output is connected to the negative input of a comparator 150. The output from analog flow signal control potentiometer 133 is connected to the positive input of comparator 150. Comparator 150 thus produces an output when ramp voltage is less than the output from flow signal control potentiometer 133. The output from comparator 150 is connected to the base of a transistor 155 which acts as an "AND" gate. A single frequency oscillator X2 has its output connected to the collector of transistor 155, which, in this embodiment, conducts pulses from oscillator X2 when enabled by the output of comparator 150 at its base. A number of pulses are thereby connected to frequency divider 136 which are indicative of equivalent minutes of preset maximum fluid flow channel 13. As pointed out above, the shaft of servo motor 127 traverses the same angle of rotation for a preselected maximum flow level in channel 13 by means of maximum level adjust 141 which adjusts gain in servo control 126. Fine adjust to assure that the output of analog flow signal potentiometer 133 may swing from the low end of output from ramp generator X1 to the high end is afforded at adjust pots R1 and R2 connected to the high and low ends of flow signal potentiometer 133 respectively.

Servo control circuit 126 is connected to a servo motor drive circuit 152 for driving cams 143 mounted on the shaft of servo motor 127. Note that a voltage regulator 153 is provided to excite potentiometers 129, 123, and 133 with a stable excitation voltage.

FIG. 10 shows a configuration for a control panel 154 on control module 38 in sampler 16. Panel 154 shows time interval switch 108, multiple container selection switch 104, multiple sample selection switch 106, mode switch 53, manual purge switch 111, manual cycle 52, and manual advance switch 109. FIG. 11 shows a control panel 156 on flow meter 24. A chart 157 is shown mounted on a rotating time base disc 158. Chart 157 is contacted by an ink-carrying pen on arm 159. An aperture 161 is provided which affords access to the slotted disc 147 upon which is displayed an indication by number of the cam 143 and follower 144 which are selected for engagement. Total flow indication is provided through a window 162 displaying the total flow in equivalent minutes of full flow through channel 13 on totalizer 137. A switch 163 is provided so that flow meter 24 may be de-energized, set in normal operation, or set to retract probe 27 to the flowmeter lower case 114, and to provide a powered condition for calibration. Sample interval selector switch 138 is also located on panel 156 as well as visual level indicator 124, and percent flow indicator 132. Maximum level adjust potentiometer 141 has associated therewith a control know 164 for setting instantaneous flow indicator 132 during calibration.

A typical operating sequence of the flow meter 24 and the sampler 16 will now be described. With power available to the flowmeter 24 a calibration is undertaken at any convenient place such as a laboratory, installation engineers office, or on the installation truck. Referring to FIG. 11, switch 163 is set to the "calibrate-return" position. The desired cam is selected by positioning slotted disc 147 in the appropriate detent so the desired cam indication number appears through aperture 161. The existing total on the totalizer is recorded. Level indicator 124 is set to display the maximum flow height to be seen in channel 13. Maximum level adjust potentiometer is set by means of control knob 164 to provide a reading of 100% at instantaneous per cent flow indicator 132 for open flow channels. For closed flow channels, such as round pipe for example, control 164 is turned past 100% in the same direction until the characteristic number of the flow channel appears. The characteristic number is the ratio of full pipe flow rate to maximum pipe flow rate, which exists when, the pipe is less than 100% full all other flow conditions being identical. The characteristic number for round pipe is 92.6%. A sample interval is calculated and selected at selector 138. Sampler 16 and flow meter 24 are mounted in the vicinity of a flow to be monitored, as is illustrated in FIG. 1 for one flow metering purpose. Intake 19 is placed within the fluid flow 21 and probe 27 is lowered to contact the surface of the flow by setting flow meter select switch 163 to the operate position. Existing flow depth in channel 13 is measured by any convenient means. Measured level is set manually at the visual level indicator 124. Flow meter 24 is now in condition for operation.

As the surface of flow 21 rises and falls, the probe 27, which is alternately engaging and disengaging the surface of flow 21, rises and falls with it. The instantaneous flow level is presented visually at indicator 124. The instantaneous flow rate is presented on Chart 157 and at flow rate indicator 132 in per cent of maximum.

Level sensor potentiometer 123 is driven by reel 119 and provides an electrical input to servo control 126, as described above. The control knob 164 sets maximum height into adjust potentiometer 141 which also produces an output delivered to servo control 126. Maximum level adjust potentiometer 141 provides for the same maximum angle of rotation of the output shaft of servo motor 127 for varying maximum outputs from level sensor potentiometer 123 due to varying expected maximum flow surface heights.

Mechanical head to flow conversion is provided by cams 143 and followers 144. The conversion may be made from height to flow measurement for any type of pipe, flume or weir. Each cam 143 is specifically designed to accommodate one general cross section shape of flow channel. The flow through a v notch weir, for example, is equal to the product of a constant times the level of flow at the weir raised to the five halves power. Flow past a flume is equal to a constant times the level at the flume raised to the three halves power. Other channel cross sectional shapes have known relationships between flow and flow level at the section. Once flow as a function of flow level is known, a cam may be constructed using well known methods and positioned on a shaft to provide motion of a cam follower which is related to flow rate when rotation related to the flow level is imparted to the shaft.

As mentioned above the shaft of potentiometer 133 is driven by the output side of the head to flow converter 128. The output from potentiometer 133 provides a voltage for controlling the pulse output from flow proportional pulser 134. The output frequency divider 136 to provide an output to total flow counter 137 which indicates flow in equivalent minutes of full flow through the channel. The total flow volume is obtained by multiplying the difference between original and existing equivalent minutes of full flow on the counter 137 by the full flow rate per minute through the particular channel 13. The output from divider 136 is also provided to sample interval selector 138 which in turn provides an output at selected multiples of minutes of full flow or flow volume quantities. The output from sample interval selector 138 actuates relay 139 and provides a flow volume indication signal for connection to the input of sampler 16. Flow meter 24 thus measures the head in the flow channel mechanically, and is adjustable to set servo control gain to provide full servo motor rotation for any maximum height of flow 21, which rotation is in linear relationship with the flow head. Flow meter 24 mechanically converts head to flow by driving a preselected cam corresponding to the cross sectional shape of the flow channel mounted on an input shaft and providing a cam follower motion for the output. The cam follower motion is used to record the flow, provide a visual readout of the instantaneous flow, total the flow, and provide a signal for use in initiating a sampler sequence.

Turning to the operation of the sampler portion of the system, reference is made to FIG. 10. The operational mode for the sampler 16 is selected at mode switch 53. With mode switch 53 in the flow position and flow meter 24 electrically connected to sampler 16, the input signal for starting a sampling sequence is provided by the flow meter as mentioned above. The signal is presented at predetermined increments of flow as selected at the sample interval selector 138 on flow meter panel 156. For example, if a channel flows at 60 gallons per minute when full, and a sample is desired after each 480 gallons of flow, the sample interval selector 138 is set to 8. This provides a sample at each 8 times 60 gallons, or 480 gallons, of flow.

Depending upon the requirements of the flow monitor program, a specific number of samples to be deposited in each storage container 43 may be selected at switch 106. In this embodiment from one to five samples may be deposited in a single container 43 before the sampling sequence will advance fill arm 99 to the subsequent container 43. In the event the flow monitoring purpose requires immediately successive identical samples to be deposited in several storage containers 43, a selection may be made at switch 104 to deposit such samples in from one to four adjacent storage containers 43. A single input signal to sampler 16 will initiate the number of sampling cycles selected at switch 104 so as to deposit a sample in the selected number of bottles or containers 43.

Without regard for the position of mode switch 53, a manual purge cycle may be initiated by depressing purge switch 111. A samplingsequence cycle may be initiated manually also at any time by depressing manual cycle switch 52. Fill arm 99 may be advanced to overlie the next adjacent container 43 when desired by depressing manual advance switch 109.

The input signal to the sampler 16 is in the form of a pulse and is connected to the initiate latch 103 in power circuit 54 which provides a power output therefrom. Power circuit 54 energizes compressor control circuit 56 seen in FIGS. 3 and 5 which drives compressor 86 seen in FIG. 4. Two-cycle timer 57 is energized and the first cycle is initiated. Two-cycle timer 57 is located in control module 101 and directs solenoid valve control 58 to actuate pressure control valve 91 to place positive pressure port 87 in communication with the interior of sample chamber 39 through line 92. This purges sample chamber 39 through pipe 73 and intake 19. After a 15-second purging period, two-cycle timer 57 energizes solenoid valve control 58 to actuate pressure control valve 91 to place negative pressure port 88 in communication with the interior of sample chamber assembly 39. The negative pressure in chamber 39 causes a sample to be drawn through intake 19, tube 22 and vertically adjustable pipe 73.

Pipe 73 is adjusted vertically in top cover 74 so that the desired volume of sample may be contained in chamber 39 between the lower end of pipe 73 and the bottom of chamber 39. Negative pressure is maintained in chamber 39 for a maximum of 30 seconds in this phase of the first cycle initiated by timer 57. As chamber 39 fills the sample level rises above the lower end of pipe 73 toward the top cover 74. The upper surface of the sample contacts electrical contact means or fill level sensor 76 depending from cover 74. Fill level sensor 76 terminates sample intake in chamber 39 through two-cycle timer 57 and solenoid valve control 58 which actuates pressure control valve 91 to remove negative pressure port 88 from communication with chamber 39.

In the event intake 19 is clogged or the flow channel 13 is dry, sample chamber 39 may not contain sufficient sample volume to bring the upper surface of the sample in contact with fill level sensor 76 within 30 seconds. In such a case, two-cycle timer 57 begins its second cycle by initiating a signal which results in actuation of pressure control valve 91 to provide positive pressure to chamber 39 for purging for fifteen seconds. Subsequently negative pressure is reintroduced into chamber 39 as before for drawing a sample into chamber 39.

Since there is a chance that some sample remained in chamber 39 below the end of pipe 73 at the end of the second purge cycle, there is a possibility that the sample chamber will be filled to contact the fill level sensors 76 during the second intake cycle, which will then terminate the fill of chamber 39 as described above. When either fill level sensor 76 is contacted or 30 seconds have passed after the second cycle in this phase of the sampling sequence, a signal is provided to the fill and measurement timer 59 with or without a full sample chamber 39. Pressure control valve 91 is actuated to place positive pressure port 87 in communication with chamber 39 for a period of 7 seconds which purges chamber 39 through pipe 73 and intake 19 until the surface of the sample is at the level of the lower end of pipe 73. The predetermined sample volume is now contained in sample chamber 39. Timer 59 signals sample valve control 61 to actuate sample control valve 96 to the open position which allows the predetermined sample volume to flow through sample outlet tube 93 to the sealed rotary union 94 and fill arm 99 to be deposited through the top openings 44 in storage containers 43 as determined by the selections made at switches 106 and 104 described above. Fifteen seconds is allowed for filling the sample containers 43 after which a signal is provided to the final purge timer 62 which begins a 5-second timing cycle. Positive pressure is again directed through pressure control valve 91 to chamber 39 for the final purge period in which intake 19 and tube 22 are cleared. Sample chamber 39 has been emptied during the previous 15 second period of time during which sample control valve 96 is open. At the end of the 5-second final purge, two-cycle timer 57 is reset by a signal from final purge timer 62. The output of final purge control timer 62 is also directed to the multiplecontainer multiplexing circuit 64 and the multiple sample multiplexing and fill arm advance circuit 63 for depositing a single sample in a preselected number of storage containers 43 or for depositing a preselected number of samples in a single storage container 43, as selected by switches 104 and 106 respectively. Fill arm advance circuit 63 produces a pulse which is counted in fill arm step count circuit 67 and which is also connected to fill arm step control circuit 66 for energizing stepping motor 97 to advance fill arm 99 to overlie the adjacent storage container 43. The advance of fill arm 99 is the ultimate step in a single sampling sequence.

A ball check valve 82 as seen in FIG. 4 is provided immediately below the top cover 74 to protect the pressure line 92, pressure control valve 91 and compressor 86. Should the fill level sensor 76 fail to function as designed and terminate the negative pressure in chamber 39, the chamber would continue to fill until the fluid sample was drawn through passage 81 and inlet pressure tube 77 into pressure line 92. To prevent this, ball check valve 82 is provided to rise with the upper surface of the sample and to seat when the fill level rises to a point near top cover 74 to block the negative pressure and terminate filling of sample chamber 39.

The next signal generated by flow meter 24 indicating that the next preselected increment of flow has passed through channel 13, initiates another sampling sequence as described above. Each sampling sequence is recorded in the fill arm step count circuit 67 until a predetermined number of advance steps have been taken by fill arm 99. In one embodiment of the disclosed invention, 24 storage containers 44 are provided and fill arm step count circuit 67 produces an output which is connected to power switch 54 after 24 such steps have been recorded. Power switch 54 is inhibited by the output from circuit 67 blocking further sampler sequencing so that no more samples may be taken until the sampling unit is attended by an operator. This prevents undesired sample dilution which would occur if fill arm 99 were allowed to traverse 360° or more.

The sampling sequence described above may have a time base as opposed to a flow quantity base by selecting mode switch 53 to the "time" position. In the time mode, switch 108 is positioned to select the time periods at the ends of which the sampling sequence will be initiated. In the present embodiment, time intervals ranging from one-quarter hour to 24 hours are selectable. Clock 51, seen in schematic detail in FIG. 5, includes a crystal oscillator X1 for providing a frequency output which is divided to produce a pulse at predetermined periods of time. The time interval for the pulse is selected at switch 108, which then delivers the pulse as the appropriate input signal to initiate the sampling sequence for collecting flow samples at the selected intervals of time. The remaining operation when in the time mode is similar to that described for the flow mode above.

A block diagram of another embodiment of the disclosed invention is shown in FIG. 12. The difference between the embodiment of FIG. 12 and that of FIG. 3 is partially due to the fact that the sampler described therein has only a single storage container 166 as seen in FIG. 13. For this reason, the diagram of FIG. 12 does not have a multiple sample and fill arm advance circuit 63, a fill arm step count circuit 67, a multiple container multiplex circuit 64, or a fill arm step control circuit 66. The remainder of FIG. 12 is similar to FIG. 3 and like elements are assigned the same item numbers.

Referring to FIG. 13, sample chamber assembly 39 is shown having vertically adjustable pipe 73 connected to the adapter 48 on tube 22. A probe 167, or plurality of probes 167, is positioned to extend into the interior of chamber 39. Probe 167 carries a sensing element which is connected to a sensing control circuit 168 which provides an output connected to a recorder 169. Compressor 86 has positive and negative pressure outlet ports 87 and 88 respectively which are directed to pressure control valve 91 and subsequently to the interior of chamber 39 through additional pressure line 92. Controlmodule 101 is connected through conductors 102 to compressor 86, pressure control valve 91, sample control valve 96, and fill level probe 76, as described in FIG. 4 above. Sample chamber assembly 39 includes a ball check valve 82 near the top of the chamber and a sample outlet tube 93 from the sample chamber base 78. Chamber 39 has a clear cylindrical wall 71 as described in FIG. 4. Sample outlet tube 93 has an extention 171 leading from the down-stream side of sample control valve 96 to the inlet for the single storage container 166.

A transient flow characteristic occurs when some substance is added to the fluid flow suddenly to produce a high transient concentration of the substance which would be diluted by pooling samples in a single container. A degradable flow characteristic occurs when a substance is added continuously or suddenly and the substance is of a character such that its presence in the fluid flow is limited in time. Volatile substances or substances which precipitate or otherwise escape from the samples will produce degradable characteristics. Transient flow characteristics may be detected by the embodiments of FIGS. 4 or 13, whereas degradable characteristics may be detected reliably only by the embodiment of FIG. 13.

Thus the operation of the embodiment shown in FIGS. 12 and 13 involves sampling for detecting transient or degradable flow characteristics. Hyper-acidity, high base concentrations, chemical contaminants, or present measurements of volatile contaminants may be made. As many probes 167 as are necessary to monitor all of the flow characteristics of this nature are mouned in the chamber 39 for contact with the flow sample as it is drawn into sample chamber 39. Dwell time of the sample in chamber 39 may be extended by adjustment at fill and measure timer 59 as necessary for measurement of the transient or degradable flow characteristics. The sampling sequence is initiated in the same manner as described for the embodiment of FIG. 3. An input is provided based on time, flow or a manually initiated input signal for beginning the sampling sequence by energizing power switch 54. Compressor 86 is turned on and two-cycle timer is initiated. As described above, sample chamber 39 is first purged for fifteen seconds followed by a 30-second maximum fill period. When the sample in chamber 39 contacts fill level probe 76 the sequence progresses to purge the chamber 39 so that only a volume below the lower end of pipe 73 remains therein. Sample control valve 96 is then energized open to allow the sample volume to drain into storage container 166 through sample outlet tube 93 and extension 171. Positive pressure is introduced into chamber 39 for a 5-second period thereafter to assist sample drain and to provide a final range through pipe 73, tube 22, and intake 19. At the end of the 5-second final purge, the 2-cycle timer 57 is reset and the sampler is in condition for another sampling sequence to be initiated by the ensuing appropriate input signal as selected at either switch 53 or 52.

As the sample level rises in sample chamber 39 during the fill period, it immerses probe 167 which senses a predetermined characteristic in the flow sample and conducts an appropriate signal to sensor control circuit 168. Sensor circuit 168 conditions the sensed signal for presentation to recorder 169 which provides a permanent time base recording of the characteristic being monitored. A plurality of probes 167, sensor control circuits 168, and recorders 169 is envisioned for as many characteristics of the flow as may be desired for monitoring.

Referring to FIG. 14 an additional embodiment of the sample chamber 39 is shown. A level sensor 172 is shown positioned so as to sense the level of the fluid inside chamber assembly 39, but which does not contact the fluid sample contained therein. A capacitance type device, for example, may serve as levelsensor 172. Level sensor 172 may be adjusted in vertical position on rod 173 and secured in a particular vertical position by means such as knurled nut 174. FIG. 14 also shows a sample fill pipe 176 which extends from the top cover 74 of sample chamber 39 to a fixed position spaced from sample chamber base 78. An elongateslot 177 is formed in the portion of sample fill pipe 176 which extends into the interior of sample chamber assembly 39. A sleeve 178 is slidably fitted to the exterior of fill pipe 176 for vertical positioning thereon. A hole 179 is formed in sleeve 178 and is aligned with elongate slot 177. A set screw 181 is threadably engaged in a hole (not shown) passing through sleeve 178 for bearing against sample fill pipe 176 to fix sleeve 178 in a preselected vertical position thereon.

The sample chamber assembly 39 of FIG. 14 is designed to operate in the following fashion. Sleeve 178 is adjusted in vertical position on fill pipe 176 until hole 179 defines a predetermined sample volume between the levels of hole 179 and the sample chamber base 78 within cylinder 71. Sleeve 178 is fixed in the desired position by turning set screw 181 until it bears against fill pipe 176. When hole 179 is aligned with elongate slot 177 fluid purged from sample chamber 39 during the pressure phase after filling, will be forced out fill pipe 176 until the level falls to the preselected level of hole 179. Pressure will not bleed from the sample chamber through hole 179, slot 177, fill pipe 176 and tube 22. In this fashion a fluid sample is introduced into sample chamber 39 at the bottom thereof with a minimum of splashing and therefore a minimum of additional oxygen being dissolved into the sample influx. Such additional oxygen solution caused by splashing when the lower end of fill tube 176 is positioned at a considerable height above base 78, may lead to test analyses which are misleading in determining the nature of the sample drawn.

Level sensor 172 is shown exterior of the cylinder 71 so as to free it from contact with the fluid sample in chamber 39, whereby it will not be fouled by caustic samples or samples containing a high density of foreign matter. Level sensor 172 is adjusted vertically on rod 173 and fixed in the desired vertical position by knurled nut 174 just above the level of hole 179, Whenever hole 179 is adjusted in vertical position to provide a new sample volume in chamber 39, level sensor 172 is similarly adjusted to assume a vertical position a minimal distance above hole 179. This type of structure reduces the possibility of heavy sedimentary material settling out of the sample during influx of the sample, and consequent purging of the lighter constituents of the sample during the purge phase which brings the sample level down to the level of hole 179. Without the proximity of levels between level sensor 172 and hole 179 a disproportionate amount of heavy sedimentary material in the sample may remain after purging thus providing misleading results in an analysis of the drawn sample. It is to be emphasized that the lower end of sample fill pipe 176 is positioned at a fixed distance above base 78 which allows unimpeded sample influx and eflux, and which may be found empirically for a given fluid being sampled, and that level sensor 172 is to be positioned at a level only slightly above the level of hole 179. Any one of a number of means are envisioned for positioning an aperture similar to hole 179 vertically along fill pipe 176 for breaking the eflux of sample from chamber 39 during the pressure or purge phase which determines the sample volume.

Reference is now made to FIG. 5 for the description of circuit elements which provide an additional embodiment of the sample disclosed herein responsive to overflow level. A connection exists between the output of clock 51 and the input of power switch 54. A float switch (not shown) of conventional design is provided for actuation by the surface level of the flow in an overflow channel. When switch 53 is selected to the "flow" position the float switch is connected betwen terminals 182 and 183. Float switch provides closure for overflow channel flow surface levels above a predetermined level. In this manner an input is provided to power switch 54 when terminal 182 is connected to ground potential. Repeated cycling is provided for repeated sampling as the input terminal on clock 51 is also connected to ground potential. In this fashion fluid samples are drawn from an overflow channel for the period during which the overflow channel exceeds a predetermined flow level. It has proven to be of interest to monitor the sample content during such high overflow periods.

A functionally diversified flow meter and sampler combination has been disclosed which provides sampling as a function of time, as a function of flow volume, as manually selected, or as a function of high flow level in an overflow channel. Accurate sample sizes are provided which are adjustable through desired ranges, and reliability of sample size and content is assured by features reducing sample characteristic change and sample size variation during sample taking periods.

We claim:

1. In a system of the type described for communication with a fluid
    means for measuring a predetermined volume of fluid, said means for measuring including a sample chamber, a level sensor for determining a predetermined fill level in said chamber and mounted outside said chamber, a fill tube member projecting into said chamber having an open end in communication with said chamber in fixed position closely spaced to the lower boundary of said chamber whereby influx and eflux through said open end is unimpeded by suspended solids in the fluid, said fill tube member having an opening in the side thereof spaced above said open end, and means for adjusting said opening in vertical position,
    means cooperating between said measuring means and said fluid to provide for transfer of fluid therebetween,
    and means for selectively operating said measuring means to purge said measuring means, fill said measuring means, measure said predetermined volume, transfer said predetermined volume, and final purge said measuring means thereby providing sampling of the fluid.

2. A system as in claim 1 together with a positive and negative pressure source and a pressure control valve connected thereto, and wherein said measuring means is connected to said pressure control valve, said means cooperating between said measuring means and said fluid including an intake tube connected to said fill tube member, and wherein said means for selectively operating said measuring means includes timing means programmable to connect said positive and negative pressure source alternately through said pressure control valve to said sample chamber.

3. A system as in claim 1 together with means for providing positive and negative pressure, a pressure control valve in communication with said means for providing pressure and with said measuring means, a sample control valve in communication with said measuring means, means for adjusting the vertical position of said level sensor to assume a position immediately above said opening said fill tube member, and storage means in communication with said sample control valve.

4. A system as in claim 3 wherein said means for selectively operating said measuring means is actuated by an electrical input signal and includes timing means for actuating said pressure control valve for alternately connecting said positive and negative pressure to said means for measuring so that said transfer of said predetermined volume is made to said storage means.

5. A system as in claim 4 together with a flow meter for providing said electrical input signal at predetermined flow volume intervals.

6. A system as in claim 4 together with a clock for providing said electrical input signal and means for selecting said electrical input signal to appear at predetermined intervals of time.

7. A system as in claim 4 together with float actuated switch means for providing said electrical input signal at predetermined flow levels.

8. A system as in claim 5 wherein said flow meter includes means for measuring head in a flow channel, and a mechanical head to flow converter connected to said means for measuring head.

9. A system as in claim 5 together with means for selecting said predetermined flow volumes.

10. A system of the type described in claim 1 together with
    means mounted in said measuring means for contacting said predetermined volume of fluid and measuring a predetermined degradable characteristic therein,
    and means for recording said degradable characteristic.

11. A system as in claim 10 wherein said means for selectively operating said measuring means to transfer said predetermined volume includes means for delaying said transfer whereby said means for measuring a degradable characteristic is in contact with said volume of fluid for an extended time period so that said degradable characteristic may be accurately measured.

12. A system of the type described in claim 1 together with
    means mounted in said measuring means for contacting said predetermined volume of fluid and measuring a predetermined transient characteristic in the fluid.

13. A system of the type described in claim 12 together with
    single storage means, means for recording said transient characteristic, and means for communicating said predetermined volume of fluid with said single storage means.

14. A system as in claim 12 wherein said means for selectively operating said measuring means to transfer said predetermined volume includes means for delaying said transfer, whereby said means for measuring a transient characteristic is in contact with said volume of fluid for an extended time period so that said transient characteristic may be accurately measured.

15. A system of the type described in claim 12 together with a plurality of storage means, and means for programming communication of said predetermined volume of fluid with separate ones of said plurality of storage means, whereby said transient characteristics are preserved in said predetermined volume of fluid.

16. In a fluid flow measuring system having a flow sampler actuated by a power source and responsive to an input signal including
a flow meter for providing the input signal,
means connected to the power source for providing positive and negative pressure,
a sample chamber for measuring a predetermined fluid sample volume in communication with said means for providing positive and negative pressure,
a fill sensor for sensing when said sample chamber is filled to a level at least as great as said predetermined sample volume, said fill sensor being located externally of said sample chamber, whereby fouling of said fill sensor by caustic samples or foreign matter therein is prevented,
said fill sensor operating to terminate negative pressure in said sample chamber and to initiate positive pressure therein, thereby expelling fluid through said means for communicating so that the fluid volume in said sample chamber is reduced to said predetermined sample volume,
means for communicating the fluid flow with said sample chamber,
means for storing said predetermined sample volume,
means for transferring said predetermined sample volume from said sample chamber to said means for storing, and timing means for providing a sampling sequence cycle, said timing means connected to said means for providing pressure, said sample chamber, and said means for transferring, whereby said positive and negative pressure is alternately communicated with said sample chamber to purge, fill and measure a sample therein, and to transfer the sample to said means for storing.

17. A fluid flow measuring system as in claim 16 wherein said means for storing includes a plurality of containers and said means for transferring communicates with said plurality of containers in sequence, and wherein said timing means includes reset means on completion of a sampling cycle, means for selecting a predetermined number of sampling cycles for each input signal, and means for selecting a predetermined number of samples for transfer to each container.

18. A fluid flow measuring system as in claim 17 together with counting means for recording the number of containers to which samples are transferred, said counting means producing an output signal after a predetermined count, said output signal being connected to said timing means for inhibiting said sampling cycle.

19. A fluid flow measuring system as in claim 16 wherein said flow meter includes a fluid head sensor, servo means driven by said head sensor, and a mechanical head to flow converter driven by said servo means, said flow meter including an electrical adjustment to said servo means for providing head to flow conversion for channels of a given cross section shape and having various shape sizes.

20. A fluid flow measuring system having a flow sampler actuated by a power source and responsive to an input signal comprising a mechanical head to flow converter including a plurality of cams and cam followers for converting head in flow channels of a plurality of predetermined cross section shapes to flow therein, and means for selecting one of said cams to engage one cam follower, servo means driven by said fluid head sensor, a mechanical head to flow converter driven by said servo means,
means connected to the power source for providing positive and negative pressure,
means for measuring a predetermined fluid sample volume, in communication with said means for providing pressure,
means for communicating the fluid flow with said means for measuring,
means for storing said predetermined sample volume,
means for transferring said predetermined sample volume from said means for measuring to said means for storing, and timing means for providing a sampling sequence cycle, said timing means connected to said means for providing pressure, said means for measuring, and said means for transferring, whereby said positive and negative pressure is alternately communicated with said means for measuring to purge, fill, and measure a sample therein, and to transfer the sample to said means for storing.

21. A fluid flow measuring system comprising a flow sampler responsive to an input signal comprising a framework, compressor means for providing positive and negative pressures at separate pressure ports thereon, a sample chamber mounted on said framework and having upper and lower limits for defining a total volume to be contained therein, means communicating between said sample chamber and the fluid flow, said means communicating including means having a lower portion fixed in position relative to said sample chamber lower limit for depositing the sample influx as close to said lower limit as possible while allowing the suspended solids in said sample to pass, said means fixed in position having an aperture above said lower portion, a pressure control valve in communication with said pressure ports for directing positive and negative pressures alternately to said sample chamber, sample storage means communicating with said sample chamber for receiving samples from said sample chamber, and means for transferring samples from said sample chamber to said sample storage means, a sample control valve disposed in said means for transferring for controlling transfer of fluid samples, a first timer producing a first output signal sequence connected to said pressure control valve, said first output signal sequence operating to actuate said pressure control valve to direct positive pressure and negative pressure to said sample chamber for predetermined periods of time, whereby said chamber is purged and filled through said means communicating between said chamber and the fluid flow, a fill sensor mounted externally on said chamber producing an output signal when said chamber is filled to a level above said aperture, said fill sensor output signal being connected to said pressure control valve for stopping chamber filling prior to the end of said first output sequence, a second timer producing a second output signal sequence connected to said pressure control valve and said sample control valve, said second output signal sequence operating to actuate said pressure control valve to direct positive pressure to said sample chamber to purge the fluid sample through said means communicating with the fluid flow until a predetermined volume of sample remains between said aperture and said lower chamber limit, and to thereafter actuate said sample control valve to an open position for transferring said sample.

22. A fluid flow measuring system as in claim 21 together with means for reinitiating said first output signal sequence if said fill sensor output signal is not produced before the end of said first output signal sequence.

23. A fluid flow measuring system as in claim 21 together with a third timer producing a third output signal sequence connected to said pressure control valve, said third output signal sequence causing actuation of said pressure control valve to direct positive pressure to said sample chamber for a predetermined time whereby said chamber is purged and said first timer is reset.

24. A fluid flow measuring system as in claim 21 together with clock means for providing the input signal, whereby the system is time proportional.

25. A fluid flow measuring system as in claim 21 together with a manual switch for providing the input signal.

26. A fluid flow measuring system as in claim 21 together with a fluid flow meter for providing the input signal at predetermined total flow intervals whereby the system is flow proportional.

27. A fluid flow measuring system as in claim 21 together with a switch for providing an actuation signal serving as the sampler input signal, said switch providing said actuation signal when the surface of a fluid flow is above a predetermined level, whereby the system cyclically samples the fluid flow when the fluid flow surface is above said predetermined level.

28. A fluid flow measuring system as in claim 26 wherein said fluid flow meter comprises means for detecting a fluid head in a flow conduit, means for providing an output signal related to said fluid head, a servo control for receiving said signal related to fluid head, a servo motor driven by said servo control, a mechanical head to flow converter driven by said servo motor for converting head to flow in a flow conduit having a given general cross section shape, means for adjusting the gain in said servo control so that said head to flow converter may measure flow in flow conduits having a cross section similar to said given general cross section shape, and means driven by said head to flow converter for providing indication of total flow through the conduit.

29. A fluid flow measuring system as in claim 28 together with a plurality of additional mechanical head to flow converters, and means for selecting a predetermined one of said additional head to flow converters for measuring flow in a flow conduit having a corresponding known cross section shape, whereby flow may be measured in a plurality of known flow conduit cross section shapes.

30. A fluid flow measuring system as in claim 28 together with a sample interval selector whereby the input to the sampling system is passed thereto only after a predetermined flow quantity has been sensed by said fluid flow meter.

31. A fluid flow measuring system as in claim 28 together with a visual level indicator driven by said means for sensing a fluid head, and a time record of flow driven by said mechanical head to flow converter.

32. A fluid flow measuring system as in claim 28 together with a percent flow indicator driven by said mechanical head to flow converter.

33. A fluid flow measuring system comprising a flow sampler responsive to an input signal comprising a framework, compressor means for providing positive and negative pressures at separate pressure ports thereon, a sample chamber mounted on said framework and having upper and lower limits for defining a total volume to be contained therein, means communicating between said sample chamber and the fluid flow, said means communicating including means having a lower portion fixed in position relative to said sample chamber lower limit for depositing the sample influx as close to said lower limit as possible while allowing the suspended solids in said sample to pass, said means fixed in position having an aperture above said lower portion, a pressure control valve in communication with said pressure ports for directing positive and negative pressures alternately to said sample chamber, a plurality of storage containers, means for transferring samples from said sample chamber to said plurality of storage containers, a sample control valve disposed in said means for transferring for controlling transfer of fluid samples, rotatable filling means in communication with said sample control valve having an outlet overlying the mouth of one of said plurality of storage containers at a time, means for driving said rotatable fill means through advancing steps for sequentially depositing samples in said plurality of storage containers, and timing means for selectively operating said pressure control valve for filling and purging said sample chamber through said lower portion and said aperture respectively, said sample control valve for transferring said sample, said means for driving said rotatable filling means including a multiple sample multiplex selector for selecting a predetermined number of samples to be deposited cumulatively in each one of said plurality of storage containers.

34. A fluid flow measuring system comprising a flow sampler responsive to an input signal comprising a framework, compressor means for providing positive and negative pressures at separate pressure ports thereon, a sample chamber mounted on said framework and having upper and lower limits for defining a total volume to be contained therein, means communicating between said sample chamber and the fluid flow, said means communicating including means having a lower portion fixed in position relative to said sample chamber lower limit for depositing the sample influx as close to said lower limit as possible while allowing the suspended solids in said sample to pass, said means fixed in position having an aperture above said lower portion, a pressure control valve in communication with said pressure ports for directing positive and negative pressures alternately to said sample chamber, a plurality of storage containers, means for transferring samples from said sample chamber to said plurality of storage containers, a sample control valve disposed in said means for transferring for controlling transfer of fluid samples, rotatable fill communication with said sample control valve having an outlet overlying the mouth of one of said plurality of storage containers at a time, and means for driving said rotatable fill means through advancing steps for sequentially filling said plurality of storage containers, and timing means for selectively operating said lower portion and said aperture respectively, and said sample control valve for transferring said sample, said means for driving, said rotatable fill means including a multiple container multiplex selector for selecting a predetermined number of samples from said sample chamber to be deposited individually into a like number of storage containers for each input signal.

35. A method of measuring fluid flow through a conduit having a known cross section comprising the steps of sensing the height of the fluid flow upper surface to provide an indication of fluid head, controlling a servo motor relative to the fluid surface height, adjusting the gain of the servo control to provide for a predetermined servo motor rotation for a predetermined maximum relative fluid flow height, converting fluid head to flow, controlling the output of a pulse generator with the flow conversion, accumulating the output of the pulse generator to provide an indication of total flow through the conduit, and feeding back the flow conversion output to the servo motor control for providing a stable servo loop.

36. A method of measuring fluid flow as in claim 35 together with the steps of indicating visually instantaneous relative fluid flow height and flow rate, and recording indication of the total flow.

37. A method of measuring fluid flow as in claim 35 together with the steps of providing a plurality of head to flow conversion selections corresponding to a plurality of general flow conduit cross section shapes, selecting one head to flow conversion according to the specific conduit cross section in use.

38. A method of measuring fluid flow through a flow conduit having a known cross section comprising the steps of sensing the height of the fluid flow upper surface to provide an indication of fluid head, controlling a servo motor relative to the fluid surface height, adjusting the gain of the servo control to provide for a predetermined servo motor rotation for a predetermined maximum relative fluid flow height, converting fluid head to flow, controlling the output of a pulse generator with the flow conversion, accumulating the output of the pulse generator to provide an indication of total flow through the conduit, feeding back the flow conversion output to the servo motor control for providing a stable servo loop, selecting predetermined increments of flow volume through the conduit, initiating a sampling sequence at the predetermined increments of flow volume, communicating a sample chamber with a source of positive and negative pressure at the beginning of the sampling sequence, purging the sample chamber by introducing the positive pressure therein for a predetermined purge period, filling the sample chamber by introducing the negative pressure therein for a predetermined fill period, sensing the upper surface of the sample in the sample chamber when the upper surface reaches a predetermined fill level exceeding that required for a predetermined sample volume, terminating the negative pressure, purging the sample chamber by introducing positive pressure for reducing the fill to a predetermined level to obtain a predetermined sample volume, and storing the sample volume.

39. A method of measuring fluid flow as in claim 38 including the steps of purging the sample chamber for the predetermined purge period if the predetermined fill level is not sensed prior to completion of the fill period, and refilling the sample chamber by introducing the negative pressure for the predetermined fill period.

40. A method of measuring fluid flow as in claim 38 wherein the step of storing the predetermined sample volume includes conducting the sample volume obtained in each sampling sequence to one of a plurality of storage containers, controlling the number of sample volumes directed to the one storage container, conducting the subsequent sample volume to an adjacent storage container after the one container has received the control number of sample volumes, counting the number of storage containers receiving sample volumes, and inhibiting the sampling sequence after a predetermined number of storage containers have received the control number of sample volumes.

41. A method of measuring fluid flow as in claim 38 wherein the step of storing the predetermined sample volume includes the steps of providing a plurality of storage containers, selecting a number of the plurality of storage containers to receive a sample volume for each predetermined increment of flow volume, conducting the sample volumes to the selected number of storage containers, stopping the sampling sequence after the selected number of storage containers have received sample volumes, and inhibiting initiation of the sampling sequence after a predetermined number of storage containers have received sample volumes.

42. A fluid flow measuring system comprising means for detecting a fluid head in a flow conduit, means for providing an output signal related to said fluid head, a servo control for receiving said signal related to fluid head, a servo motor driven by said servo control, a plurality of mechanical head to flow converters driven by said servo motor for converting head to flow for a flow conduit having one of a plurality of given general cross section shapes, means driven by one of said head to flow converters for providing indication of total flow through the conduit, and means for selecting a predetermined one of said plurality of head to flow converters for measuring flow in a flow conduit having a corresponding known cross section shape, whereby flow may be measured in a plurality of known flow conduit cross section shapes.

43. A fluid flow measuring system as in claim 42 together with a sample interval selector whereby an output signal is generated after a predetermined flow quantity has been sensed by said fluid flow meter.

44. A fluid flow measuring system as in claim 42 together with a visual level indicator driven by said means for sensing a fluid head, and a time record of flow driven by said mechanical head to flow converter.

45. A fluid flow measuring system as in claim 42 together with a percent flow indicator connected to said mechanical head to flow converter.

46. A system for communication with a fluid comprising a fluid sampler, a sample chamber in said fluid sampler, means cooperating between said sample chamber and said fluid providing for transfer of fluid therethrough, said means cooperating including a tube disposed in said sample chamber having a lower end fixed in close relative position with the bottom of said sample chamber to deposit sample influx as close to the bottom as possible to reduce sample aeration, means for actuating said fluid sampler so that a sample of the fluid is drawn therein, a probe extending into said sample chamber for contacting the fluid drawn into said fluid sampler, said probe being sensitive to and providing a signal output indicative of predetermined substances added to the fluid, so that a substance added to the fluid which has a characteristic such that its presence in the fluid flow is limited in time is detected without sample alteration from aeration, and means for providing a signal indicative of the concentration of said substance.

47. A system for communication with a fluid comprising a fluid sampler, means cooperating between said fluid sampler and the fluid to provide for transfer of the fluid therebetween, a sample chamber included in said fluid sampler, a sample control valve connected with said sample chamber, rotatable fill means in communication with said sample control valve, a probe extending into said sample chamber contacting the fluid for detecting a substance which is diluted by pooling of samples from said fluid sampler, a plurality of storage means, means for controlling said sample control valve to an open position when said rotatable means overlies one of said plurality of storage means, and means for driving said rotatable fill means to overlie separate ones of said plurality of storage means, whereby transient characteristics in fluid samples are preserved in said separate ones of said plurality of storage means.

* * * * *